(12) United States Patent
Momot et al.

(10) Patent No.: US 6,341,957 B1
(45) Date of Patent: Jan. 29, 2002

(54) METHOD OF TRANSILLUMINATION IMAGING OF TEETH

(75) Inventors: Tomasz Momot, Ossining, NY (US); Adam Jacobs, Woodcliff Lake, NJ (US)

(73) Assignee: Electro-Optical Sciences Inc., Irvington-on-Hudson, NY (US)

( * ) Notice: Subject to any disclaimer, the term of this patent is extended or adjusted under 35 U.S.C. 154(b) by 0 days.

(21) Appl. No.: 09/722,248

(22) Filed: Nov. 24, 2000

Related U.S. Application Data

(60) Provisional application No. 60/167,711, filed on Nov. 27, 1999.

(51) Int. Cl.[7] .............................. A61C 5/00; A61C 3/00; A61C 1/00; G06K 9/00
(52) U.S. Cl. ........................ 433/215; 433/29; 382/100; 382/115; 382/128
(58) Field of Search .............................. 433/6, 29, 215; 382/100, 115, 128, 212, 218

(56) References Cited

U.S. PATENT DOCUMENTS

| | | | | |
|---|---|---|---|---|
| 5,440,393 A | * | 8/1995 | Wenz | 433/29 |
| 5,476,095 A | * | 12/1995 | Schnall et al. | 128/653.2 |
| 5,718,666 A | * | 2/1998 | Alarcon | 600/249 |
| 5,865,621 A | * | 2/1999 | Calderwood | 433/116 |
| 6,201,880 B1 | * | 3/2001 | Elbaum et al. | 382/100 |

* cited by examiner

Primary Examiner—Nicholas D. Lucchesi
(74) Attorney, Agent, or Firm—Rodney T. Hodgson

(57) ABSTRACT

An elastomeric locator held against a proximal surface of the tooth and against the gum holds a light source and imaging optics in a reproducible position for imaging a tooth in vivo.

15 Claims, 3 Drawing Sheets

METHOD OF TRANSILLUMINATION IMAGING OF TEETH

RELATED APPLICATIONS

This application is related to a copending U.S. application Ser. No. 09/670,492, filed Sep. 26, 2000 by the present inventors, and to copending U.S. application Ser. No. 08/778,001 filed Dec. 31, 1996, (now U.S. Pat. No. 6,201,880 issued Mar. 13, 2001). The present application is related to U.S. application Ser. Nos. 09/407,344 and 09/407,345 filed on Dec. 20, 1999 now U.S. Pat. No. 6,294,443 and U.S. Provisional Application No. 60/167,711 filed Nov. 27, 1999 by the same inventors as the present invention. The above identified applications which are assigned to the assignee of the present invention are incorporated herein by reference in their entirety including incorporated material.

FIELD OF THE INVENTION

The field of the invention is the field of imaging of teeth in a mouth.

BACKGROUND OF THE INVENTION

The above identified US patent applications summarize the background of the art in great detail. In brief, the prior art to the above identified applications is deficient in that images of teeth taken with light transillumination were not reproducible. The above identified applications teach that the illumination source and imaging system must be held in a reproducible and repeatable position with respect to the tooth by anchoring the source and imaging system physically with respect to the tooth. Prior art sources of light for transillumination tend to produce extraneous light scattered into an imaging system if a broad area light is used as a light source, and tend to produce non-uniform illumination if a small area light source is used.

SUMMARY OF THE INVENTION

The present invention is a method, apparatus, and system for digital imaging of teeth through transillumination of teeth in a mouth. The invention comprises using an elastomeric locator which contacts both a proximal surface of a tooth and the gum holding the tooth. The elastomeric locator is physically connected both to a light source for illuminating the tooth and to imaging optics which conduct light (which has been transmitted from the light source and through the tooth) to an image receiver such as a CCD array, a vidicon, a CMOS imaging array, photographic film, or other image receiving devices which may form an image of the tooth.

DETAILED DESCRIPTION OF THE INVENTION

Figure 1:
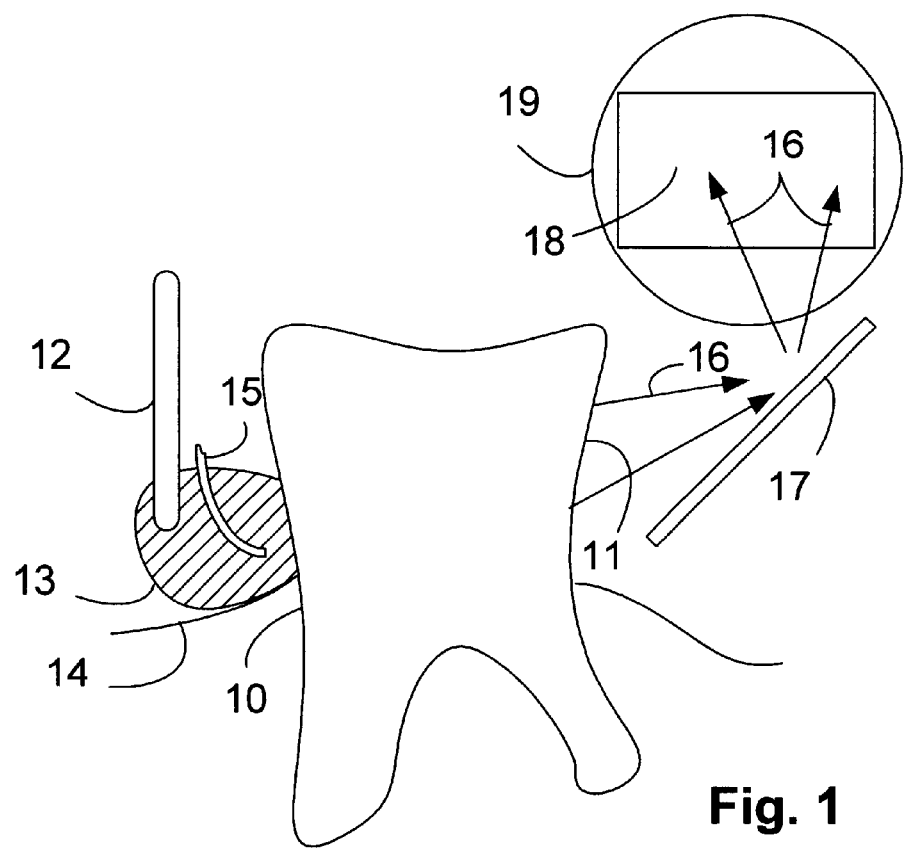
FIGS. 1 shows an embodiment of the invention

FIG. 1 shows an embodiment of the invention where a labial or lingual surface 11 of the tooth 10 is imaged. A body 12 is held in a reproducible position with respect to tooth 10 by means of an elastomeric locator 13. The locator 13 may be shaped with a V shaped groove (shown later) which fits between tooth 10 and neighboring teeth. The elastomeric locator also rests against the gum 14 holding the tooth 10 so that body 12 is held in a reproducible position. A source of light such as a light pipe 15 shines light on a labial or buccal surface of the tooth 10. The light enters the tooth and is scattered within the tooth. Some of the light 16 which is scattered in the tooth 10 exits the surface 11 of the tooth 10. We call such a process transillumination of the tooth. Light 16 exits the surface 11 and is directed to mirrors 17 and 18 held in a known position (connection not shown) with respect to body 12 by a holding means 19. Surface 11 is imaged in an imaging system (not shown) using light 16.

Figure 2:
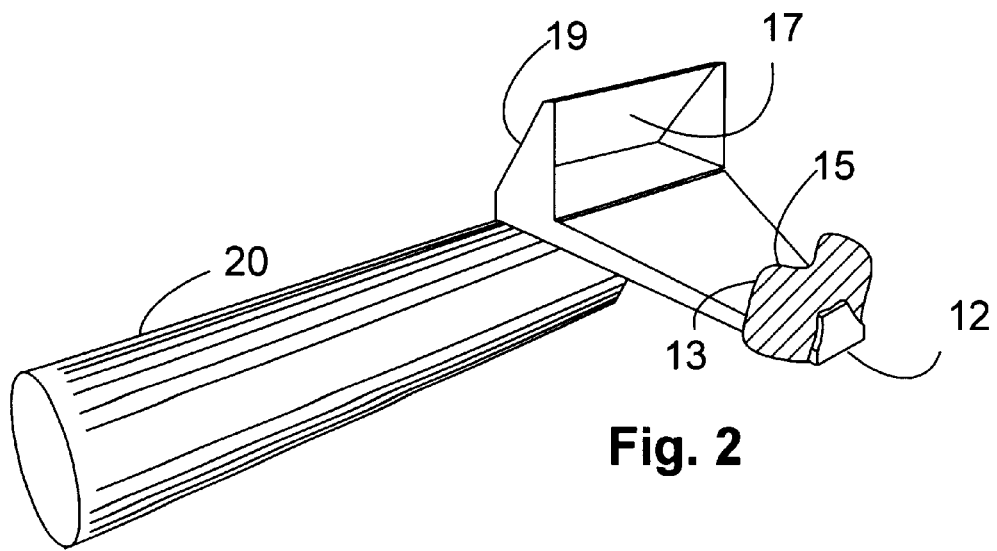
FIGS. 2 shows a perspective sketch of an embodiment of the invention.

FIG. 2 shows an adaptation of a perspective sketch of a disposable mouthpiece described in U.S. applications Ser. Nos. 09/407,344 and 09/407,345. A handle 20 for conducting light from a tooth and imaging a labial or buccal surface of the tooth while illuminating the opposite side of the tooth is shown. Light from a handpiece (not shown) is brought into the handle 20, and an optical light pipe, whose position is shown as 15 in FIG. 2, brings the light around to a position at the base of the elastomeric locator 13 from whence the surface of the tooth is illuminated. The entire body 12 holding locator 13, light pipe 15, and mirror 17 rotates around an axis perpendicular to the handle 20 so that the buccal and labial surfaces of the tooth 10 may be illuminated and imaged in turn.

Figure 3:
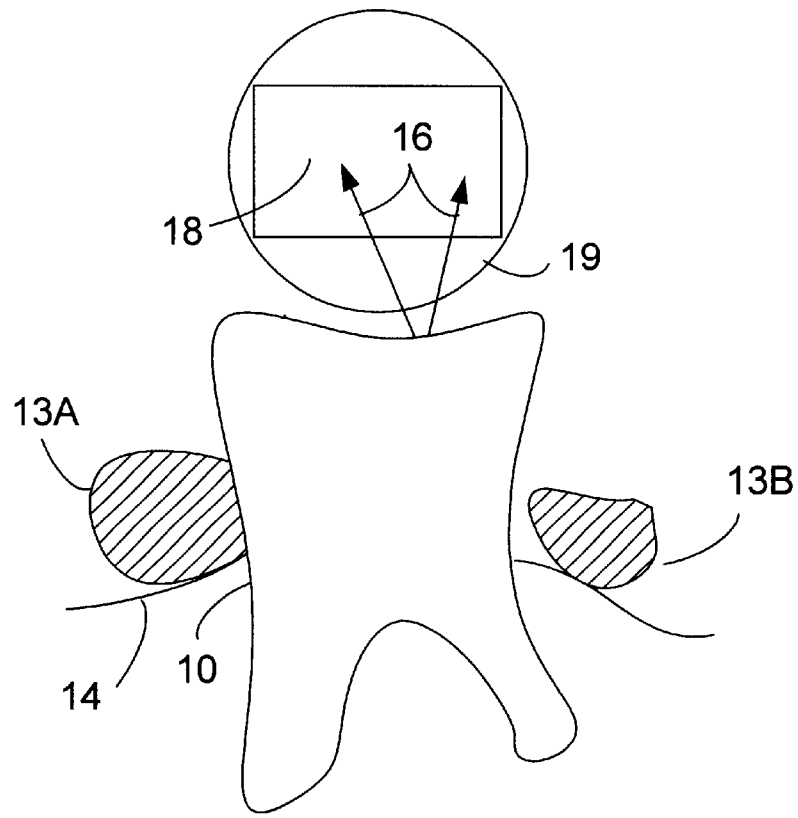
FIG. 3 shows a sketch of an embodiment of the present invention.

FIG. 3 shows a preferred embodiment of the invention, where the occlusal surface of tooth 10 is imaged using light incident from either the labial or buccal surface or from both surfaces simultaneously. In FIG. 3, two elastomeric locators 13A and 13B are shown to show that the illumination and the imaging system may be more precisely located with respect to the tooth and gum.

Figure 4:
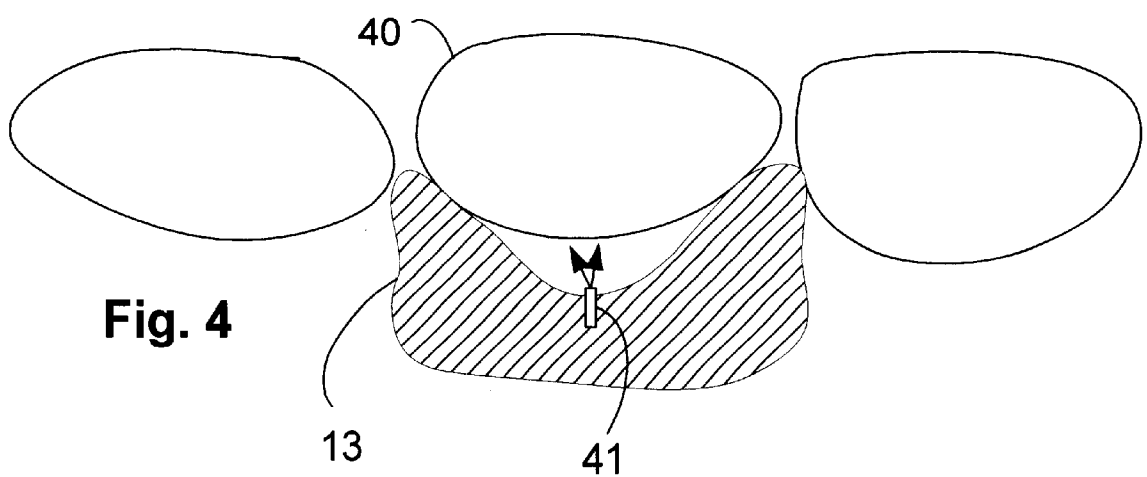
FIG. 4 is a plan view of a number of teeth "in vivo" showing the position of the elastomeric locator of the invention.

FIG. 4 shows a plan view of a preferred embodiment of the invention showing a "v" shaped elastomeric locator with the tips of the "v" contacting the proximal surfaces of tooth 40, where the light source 41 is held away from the tooth and in position to illuminate the tooth, while either the opposite surface or the occlusal surface of the tooth is imaged.

Figure 5:
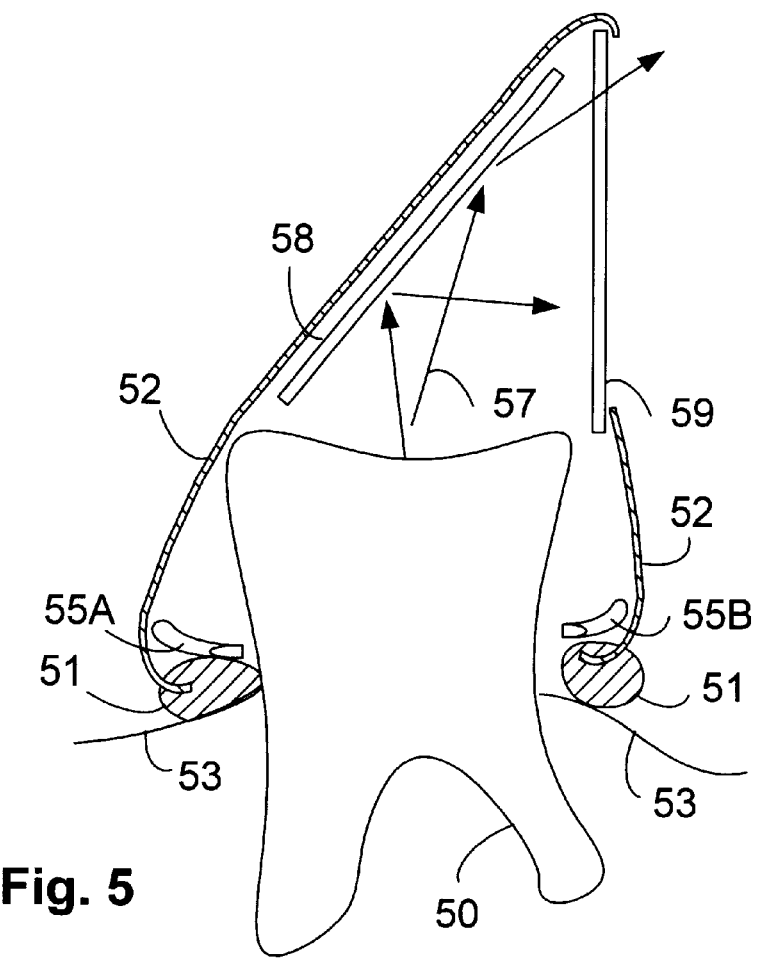
FIG. 5 is a drawing of a preferred embodiment of the invention.

FIG. 5 shows a sketch of a preferred embodiment of the invention. A holder 52 slips down over the tooth 50 and elastomeric pads 51 rest on the gum 53 and/or the proximal surfaces of the tooth 50 and holds the holder 52 reproducibly in place. Optical fibers 55A and 55B bring light from a handle (not shown) to illuminate both buccal and labial surfaces of the tooth 50. Light 57 which has been scattered in the tooth exits the occlusal surface of the tooth, strikes mirror 58, and is directed through a transparent window to an imaging system (shown later).

Figure 6:
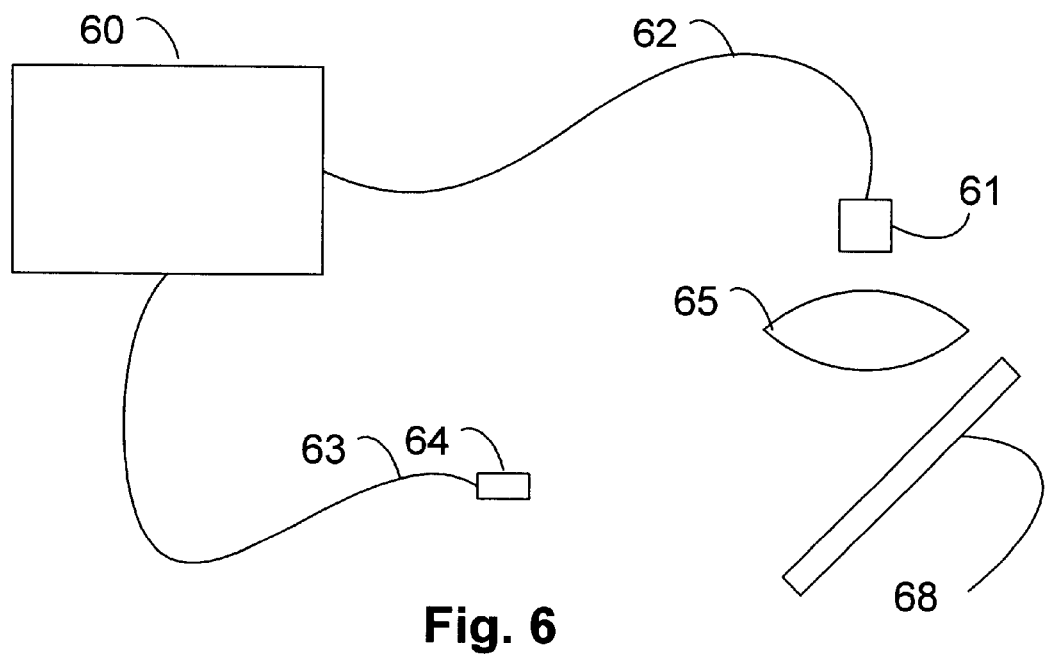
FIG. 6 is a block drawing of the system of the invention.

FIG. 6 shows a block diagram of the transillumination imaging system of the invention. Light reflected from mirror 18 or 58 may be further reflected in other mirrors 68 and finally passed through a lens 65 so that the surface of the tooth 50 is imaged on an image receiver 61. The image receiver 61 may be photographic film, a vidicon, a CCD array, or a CMOS detector, all of which are well known to those of ordinary skill in the art of imaging, or any other image detector as is known or will become known in the art of image receiving and processing. The electronic signals from an electronic image receiver may be passed over line 62 to a controller 60 which controls light from a lighting device 64 which provides light for illuminating the tooth. The signals to control the light are passed over line 63. The controller is or is connected to a computer which may display the image on an imaging device such as a computer monitor screen and/or print out images on a printer device. All of such devices as are known in the art may be included in the controller 60 or may be stand-alone devices or may be any combination of stand alone devices and integrated devices. Line 62 may be instead a wireless link. The controller 60 may further pass images or modified images to remote controllers and/or data storage and display facilities.

Obviously, many modifications and variations of the present invention are possible in light of the above teachings. It is therefore to be understood that, within the scope of the appended claims, the invention may be practiced otherwise than as specifically described.

We claim:

1. A method of transillumination imaging of a tooth in vivo in a mouth, comprising:
   a) placing an elastomeric locator in a reproducible position against a surface in the mouth; then
   b) illuminating the tooth using at least one light source held in a known position with respect to the elastomeric locator and hence in a reproducible location with respect to the tooth; and then
   c) reproducibly imaging the tooth using light from the light source which has transilluminated the tooth, wherein the imaging is performed with an imaging system held in a known position with respect to the elastomeric locator.

2. The method of claim 1, where the elastomeric locator has a "v" shaped surface for contacting a proximal surface of the tooth and holding the light source away from the tooth.

3. The method of claim 2, where the light source is a fiber optic light source.

4. The method of claim 1, where one surface of the tooth is illuminated, and the opposite surface of the tooth is imaged.

5. The method of claim 4, where a first light source and a second light source each illuminate different areas of the one surface of the tooth.

6. The method of claim 1, wherein at least the labial or the buccal surface of the tooth is illuminated, and the occlusal surface of the tooth is imaged.

7. The method of claim 6, where a first light source illuminates the buccal surface of the tooth, and a second light source illuminates the labial surface of the tooth.

8. The method of claim 1, where the elastomeric locator contacts a gum near the tooth.

9. The method of claim 8, where the elastomeric locator has a "v" shaped surface which contacts a proximal surface of the tooth and holds the light source away from the tooth.

10. An apparatus for transilluminating and imaging a tooth in vivo in a mouth, comprising;
    a) an elastomeric locator for placing against a surface in the mouth;
    b) at least one light source for holding in a reproducible location with respect to the tooth and for illuminating the tooth, the light source held in a known position with respect to the elastomeric locator; and
    c) optics for reproducibly conveying light from the light source which has transilluminated the tooth to an image receiver, wherein the image receiver is held in a known position with respect to the elastomeric locator.

11. A system for transilluminating and imaging a tooth in vivo in a mouth, comprising;
    a) an elastomeric locator for placing against at least one proximal surface of a tooth and against a gum in vivo;
    b) at least one light source for holding in a reproducible location with respect to the tooth and for illuminating the tooth, the light source held in a known position with respect to the elastomeric locator;
    c) optics for reproducibly conveying light from the light source which has transilluminated the tooth to an image receiver, wherein the image receiver is held in a known position with respect to the elastomeric locator; and
    d) an image receiver apparatus.

12. The system of claim 11, further comprising a display apparatus for displaying an image received by the image receiver.

13. The system of claim 11, further comprising storage means for storing the image received by the image receiver.

14. The system of claim 11, further comprising image transmission means for transmitting the image received by the image receiver.

15. The system of claim 11, further comprising computer means for modifying the image received by the image receiver.

* * * * *